(12) United States Patent
Wang et al.

(10) Patent No.: US 11,965,959 B2
(45) Date of Patent: Apr. 23, 2024

(54) ADAPTIVE ULTRASOUND FLOW IMAGING

(71) Applicant: KONINKLIJKE PHILIPS N.V., Eindhoven (NL)

(72) Inventors: Shiying Wang, Melrose, MA (US); Sheng-Wen Huang, Ossining, NY (US); Hua Xie, Cambridge, MA (US); Keith William Johnson, Lynwood, WA (US); Liang Zhang, Issaquah, WA (US); Thanasis Loupas, Kirkland, WA (US); Truong Huy Nguyen, Redmond, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 370 days.

(21) Appl. No.: 17/287,623

(22) PCT Filed: Oct. 14, 2019

(86) PCT No.: PCT/EP2019/077690
§ 371 (c)(1),
(2) Date: Apr. 22, 2021

(87) PCT Pub. No.: WO2020/083679
PCT Pub. Date: Apr. 30, 2020

(65) Prior Publication Data
US 2021/0373154 A1    Dec. 2, 2021

Related U.S. Application Data

(60) Provisional application No. 62/749,170, filed on Oct. 23, 2018.

(51) Int. Cl.
*G01S 15/89* (2006.01)
*A61B 8/06* (2006.01)
(Continued)

(52) U.S. Cl.
CPC ............ *G01S 15/8984* (2013.01); *A61B 8/06* (2013.01); *A61B 8/488* (2013.01); *A61B 8/5207* (2013.01); *G01S 7/52085* (2013.01)

(58) Field of Classification Search
CPC ......... A61B 8/06; A61B 8/488; A61B 8/5207; G01S 7/52085; G01S 15/8984
See application file for complete search history.

(56) References Cited

U.S. PATENT DOCUMENTS 5,769,079 A * 6/1998 Hossack ................ A61B 8/145
600/454
5,899,864 A    5/1999 Arenson et al.
(Continued)

FOREIGN PATENT DOCUMENTS

JP    2004195228 A    7/2004
WO    2004051310 A1    6/2004

OTHER PUBLICATIONS

PCT/EP2019/077690 ISR & WO, dated Jan. 20, 2020, 16 Page Document.

*Primary Examiner* — John D Li

(57) ABSTRACT

The present disclosure describes ultrasound systems configured to enhance flow imaging and analysis by adaptively adjusting one or more imaging parameters in response to acquired flow measurements. Example systems can include an ultrasound transducer and one or more processors. Using the system components, mean flow velocity magnitude and acceleration can be determined within a target region during an acquisition phase, which may include a cardiac cycle. One or more adjusted flow imaging parameters, such as adjusted ensemble length, temporal smoothing filter length and/or step size, can be determined based on the acquired flow measurements to increase the signal quality of newly acquired ultrasound echo signals. The adjusted flow imaging
(Continued)

parameters can then be applied by the ultrasound transducer during a second acquisition phase.

16 Claims, 7 Drawing Sheets

(51) Int. Cl.
*A61B 8/08* (2006.01)
*G01S 7/52* (2006.01)

(56) References Cited

U.S. PATENT DOCUMENTS

| | | |
|---|---|---|
| 6,530,885 B1 | 3/2003 | Entrekin et al. |
| 2004/0049105 A1* | 3/2004 | Crutchfield ............ G16H 50/20 600/407 |
| 2005/0131300 A1* | 6/2005 | Bakircioglu ............ A61B 8/06 600/453 |
| 2005/0197572 A1* | 9/2005 | Williams ............ G01S 7/52088 600/437 |
| 2006/0098853 A1* | 5/2006 | Roundhill ........... G01S 7/52085 382/128 |
| 2007/0016037 A1 | 1/2007 | Houle et al. |
| 2007/0112269 A1 | 5/2007 | Germond-Rouet et al. |
| 2013/0123630 A1* | 5/2013 | Freiburger ............. A61B 8/485 600/443 |
| 2014/0336510 A1* | 11/2014 | Park ..................... A61B 8/5269 600/441 |
| 2015/0045666 A1* | 2/2015 | Lin ...................... A61B 8/5223 600/441 |
| 2016/0361040 A1 | 12/2016 | Tanaka et al. |
| 2017/0086778 A1 | 3/2017 | Brandl et al. |
| 2018/0000456 A1 | 1/2018 | Wong et al. |

* cited by examiner

ADAPTIVE ULTRASOUND FLOW IMAGING

CROSS-REFERENCE TO PRIOR APPLICATIONS

This application is the U.S. National Phase application under 35 U.S.C. § 371 of International Application No. PCT/EP2019/077690, filed on Oct. 14, 2019, which claims the benefit of U.S. Provisional Patent Application No. 62/749,170, filed on Oct. 23, 2018. These applications are hereby incorporated by reference herein.

TECHNICAL FIELD

The present disclosure pertains to ultrasound systems and methods for adaptive flow imaging. Particular implementations involve systems configured to estimate mean flow velocity magnitude and acceleration, and adapt at least one flow imaging parameter in response to the velocity and/or acceleration determinations.

BACKGROUND

Ultrasound imaging systems may be operable in B mode for tissue imaging, and in Doppler or Vector Flow Imaging (VFI) modes for flow analysis and imaging. Example Doppler modes include color velocity or power Doppler mode used for both tissue motion and flow imaging, and spectral Doppler for tissue or flow quantification. Doppler can be performed in one dimensional imaging (M mode and spectral Doppler), two dimensional imaging, and three dimensional imaging.

Preexisting ultrasound systems, including acquisition-based color Doppler imaging and VFI, are not adaptive to changing flow velocity and acceleration, often rendering such systems inaccurate during pulsatile flow imaging, which refers to imaging in which the object of interest, e.g., the carotid artery, exhibits pulsatile flow instead of continuous flow. For example, preexisting systems may apply the same imaging and/or measurement parameters to slow flow and fast flow even though slow flow may be imaged/measured with greater accuracy using a different set of imaging parameters than fast flow. The frequent result is a low signal-to-noise ratio (SNR) and/or poor temporal resolution of the resulting flow images.

SUMMARY

The present disclosure describes systems and methods for enhancing flow imaging and analysis, especially of pulsatile flow, by adaptively adjusting one or more imaging parameters in response to acquired flow measurements. An ultrasound system according to embodiments herein can be configured to determine mean flow velocity magnitude and acceleration at specific spatial, temporal, or spatiotemporal windows responsive to the detected pulsatile nature of flow. Based on the determined velocity and acceleration, the system can adjust one or more flow imaging parameters, such as ensemble length and step size, respectively, to increase a SNR. The inventors recognized that faster flow requires shorter ensemble lengths to improve the temporal resolution of acquired flow information, and slower flow requires longer ensemble lengths to increase flow SNR. Accordingly, the system can decrease the ensemble length in response to higher mean velocity magnitudes, and likewise increase the ensemble length in response to lower mean velocity magnitudes. In a similar manner, higher flow acceleration values can prompt the system to decrease the step size (or lag time) between temporal samples, and lower flow acceleration may prompt the system to increase the step size. The systems described herein thus embody significant improvements over conventional interleaved, acquisition-based color Doppler imaging systems, which typically implement pre-selected, non-adjustable ensemble lengths and step sizes regardless of flow velocity and acceleration, and continuous, acquisition-based VFI systems, which are similarly limited to temporal smoothing filter lengths and step sizes that are non-responsive to flow velocity or acceleration. The fixed settings of such systems may be adequate for imaging flow of constant or relatively stable velocity, but are inaccurate when imaging pulsatile flow, such as the flow observed during carotid artery imaging, where peak flow velocity magnitudes may reach more than 200 cm/s at systole and minimum flow velocity magnitudes may dip to less than 20 cm/s at diastole.

In accordance with some examples of the present disclosure, an ultrasound imaging system can include an ultrasound transducer configured to acquire echo signals responsive to ultrasound pulses transmitted toward a target region comprising fluid flow. The system can also include one or more processors in communication with the ultrasound transducer. The processors can be configured to determine flow properties of the fluid flow within the target region based on groups of echo signals acquired during a first acquisition phase. The processors can also be configured to determine adjusted flow imaging parameters based on the flow properties. The system can also include a beamformer coupled with the ultrasound transducer and configured to apply the adjusted flow imaging parameters to a next group of echo signals acquired by the ultrasound transducer during a second acquisition phase.

In some examples, the flow properties can include a mean flow velocity magnitude and an acceleration. In some embodiments, the adjusted flow imaging parameters can include an adjusted ensemble length and an adjusted step size. In some examples, the one or more processors can be further configured to determine a signal-to-noise ratio (SNR) based on the groups of echo signals. In some embodiments, the processors can be further configured to compare the SNR to a threshold value, and if the SNR is greater than the threshold value, place a hold on additional flow imaging parameter adjustments. In some examples, the system can also include a graphical user interface configured to display a selectable graphic for initiating the processors. In some embodiments, the graphical user interface can be further configured to display the flow properties and/or the adjusted flow imaging parameters. In some examples, the graphical user interface can be configured to display a SNR based on the groups of echo signals.

In some embodiments, the first acquisition phase includes about 1 to 4 cardiac cycles, inclusive. In some examples, the first acquisition phase and the second acquisition phase together can comprise consecutive cardiac cycles. In some embodiments, the groups of echo signals can include between 15 and 60 groups of echo signals per second. In some examples, the target region can include a carotid artery, a heart, a sub-region of the heart, a portion of a blood vessel, or combinations thereof.

In accordance with some examples of the present disclosure, an ultrasound imaging system can include an ultrasound transducer configured to acquire echo signals responsive to ultrasound pulses transmitted toward a target region comprising fluid flow. The system may also include one or more processors in communication with the ultrasound transducer. The processors may be configured to determine a mean flow velocity magnitude and an acceleration of the fluid flow on a frame-by-frame basis within the target region based on one or more groups of echo signals acquired during a first acquisition phase comprising at least one cardiac cycle. The processors may be further configured to determine an adjusted ensemble length and an adjusted step size based on the mean flow velocity magnitude and the acceleration of the fluid flow. The system may also include a beamformer coupled with the ultrasound transducer and configured to apply the adjusted ensemble length and the adjusted step size to a next group of echo signals acquired by the ultrasound transducer during a second acquisition phase.

In accordance with some examples of the present disclosure, a method of ultrasound imaging can involve acquiring echo signals responsive to ultrasound pulses transmitted into a target region comprising fluid flow by a transducer operatively coupled to an ultrasound system and determining flow properties of the fluid flow within the target region based on groups of echo signals. The method can also involve determining adjusted flow imaging parameters based on the flow properties and applying the adjusted flow imaging parameters to a next group of echo signals acquired by the ultrasound transducer.

In some examples, the flow properties can include a mean flow velocity magnitude and an acceleration. In some embodiments, the adjusted flow imaging parameters can include an adjusted ensemble length and an adjusted step size. In some examples, the method can also involve determining and displaying a SNR based on the groups of echo signals. In some embodiments, the method can further involve comparing the SNR to a threshold value, and if the SNR is greater than the threshold value, placing a hold on additional flow imaging parameter adjustment. In some examples, the method can also involve displaying the flow properties and/or the adjusted flow imaging parameters. In some embodiments, the method can also involve displaying a selectable graphic for initiating the determining the adjusted flow imaging parameters.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

Figure 1:
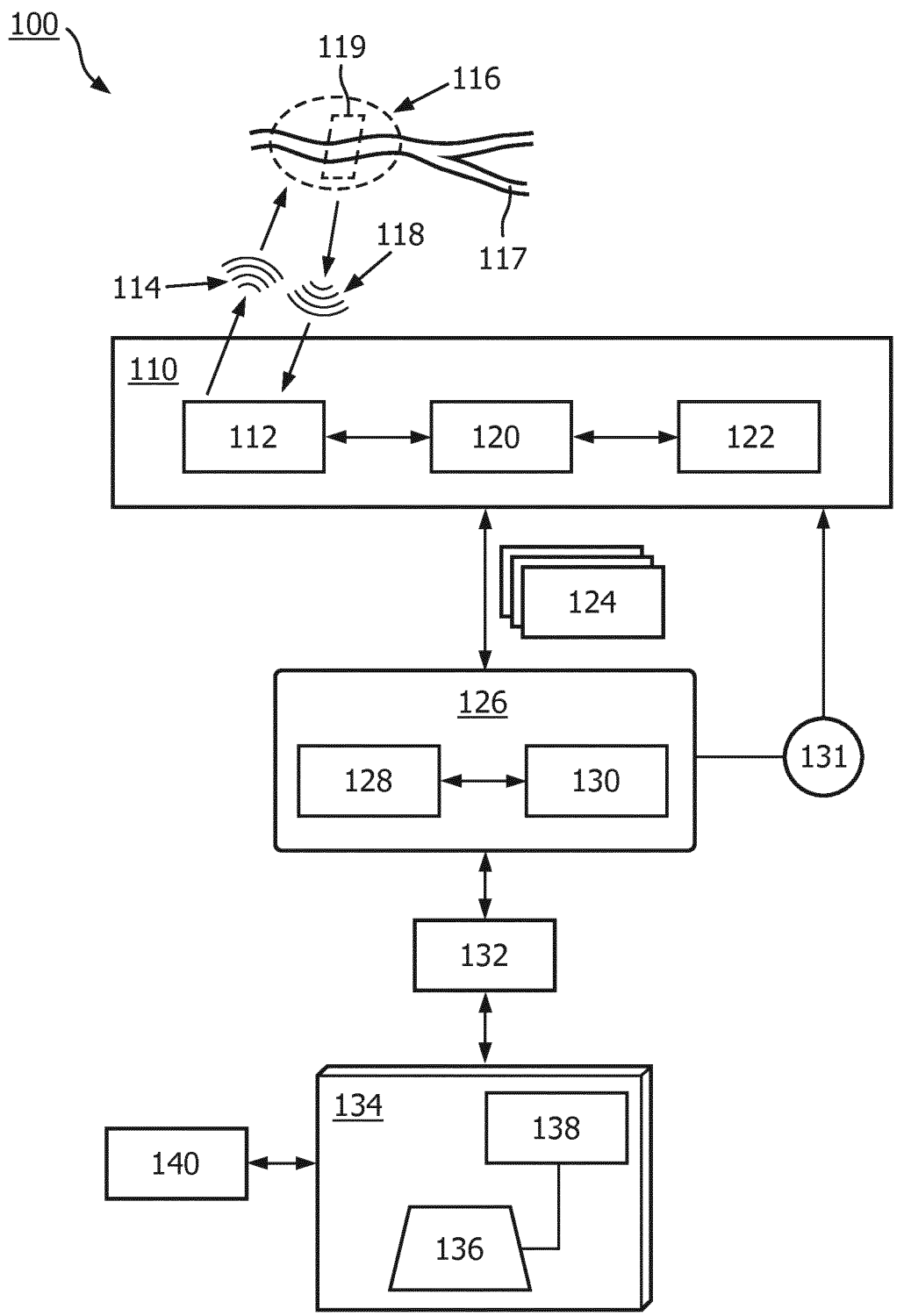
FIG. 1 is a block diagram of an ultrasound system in accordance with an embodiment of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Systems and methods herein are configured to measure and image flow, such as the blood flow within a vessel or the heart. Example systems may be configured to adaptively adjust the parameters used to interrogate flow in response to one or more measured flow properties. The parameters can include the ensemble length and step size used to examine pulsatile flow. Ensemble length can be defined as the number of temporal signal samples used for averaging flow velocity. The equivalent term in VFI is temporal smoothing size. Step size, or lag, is related to flow acceleration/deceleration and is used for autocorrelation (R1) estimation. In embodiments, the adaptive adjustments to ensemble length and step size can be applied to an assortment of targets, including blood flow, moving tissue and/or contrast agents, e.g., microbubbles. Some embodiments may be configured to operate in a continuous manner, e.g., VFI and color Doppler/CPA, while additional embodiments can be configured to operate on data stored in memory. As such, implementations can operate on a cardiac-cycle basis and/or on a real-time, loop, or time-window-by-time-window basis, or in replay or playback mode. Examples herein are described primarily with respect to Doppler applications and as such, ensemble length adjustments are specifically discussed; however, the methods herein are also compatible with additional imaging systems, including VFI.

An ultrasound system in accordance with principles of the present disclosure may include or be operatively coupled to an ultrasound transducer configured to transmit ultrasound pulses toward a medium, e.g., a human body or specific portions thereof, and generate echo signals responsive to the ultrasound pulses. The ultrasound system may include a beamformer configured to perform transmit and/or receive beamforming, a beamformer controller configured to direct beamform transmission and receipt of the beamformer, and a display configured to display, in some examples, ultrasound images generated by the ultrasound imaging system in B-mode and/or Doppler mode. The ultrasound imaging system may include one or more processors, which may be implemented in hardware and/or software components. The ultrasound system may include a display or graphics processor, which is operable to arrange the ultrasound images (2D, 3D, 4D etc.) and/or additional graphical information, which may include annotations, confidence metrics, user instructions, tissue information, patient information, indicators, color coding, highlights, and other graphical components, in a display window for display on a user interface of the ultrasound system. In some embodiments, the ultrasound images and associated measurements may be provided to a storage and/or memory device, such as a picture archiving and communication system (PACS) for post-exam review and reporting purposes.

FIG. 1 shows an example ultrasound system according to an embodiment of the present disclosure. The ultrasound system 100 may include an ultrasound data acquisition unit 110. The ultrasound data acquisition unit 110 can include an ultrasound probe which includes an ultrasound sensor array 112 configured to transmit ultrasound pulses 114 into a region-of interest (ROI) 116, which may include a blood vessel 117, and receive ultrasound echoes 118 responsive to the transmitted pulses. As further shown, the ultrasound data acquisition unit 110 can include a beamformer 120 and a signal processor 122, which can be configured to generate a stream of discrete ultrasound image frames 124 from the ultrasound echoes 118 received at the array 112. The image frames 124 can be communicated to a data processor 126, e.g., a computational module or circuitry, configured to determine mean flow velocity magnitude and/or acceleration of the fluid flow within the ROI 116. The data processor 126 may also be configured to determine adjusted ensemble lengths and/or step sizes in response to the determined velocity and/or acceleration information, respectively. In some embodiments, the data processor 126 can be configured to determine adjustments to one or more additional flow imaging parameters, e.g., wall filter settings, in response to acquired flow velocity and/or acceleration values. The data processor 126 can comprise separate modules configured to make separate determinations. For example, a flow property module 128 may be configured to determine the velocity/acceleration information within the ROI 116, and a parameter adjustment module 130 may be configured to utilize the determinations of the flow property module 128 to determine flow imaging parameter modifications, e.g., ensemble length and step size adjustments, capable of improving a SNR, thereby also improving the accuracy and/or sensitivity of the system 100. The system 100 may also include a display processor 132 and a graphical user interface 134, together configured to organize and display ultrasound images 136, data 138, and/or user notifications or elements 140.

The ultrasound data acquisition unit 110 can be configured to acquire ultrasound data from one or more ROIs 116, which may include various features including moving tissue and/or fluid flow. Specific examples described herein include the heart and carotid artery, but the disclosed embodiments are not limited to such anatomical features. In some examples, the ultrasound data acquisition unit 110 may be configured to transmit ultrasound pulses and receive the corresponding echoes within a sample volume 119 defined within the ROI 116, which may be displayed on the graphical user interface 134, e.g., overlaid on a live ultrasound image 136 of the ROI 116. The ultrasound sensor array 112 may include at least one transducer array configured to transmit and receive ultrasonic energy. The settings of the array 112 can be preset for performing an examination of tissue or fluid flow and can be adjustable during a particular scan. A variety of transducer arrays may be used, e.g., linear arrays, convex arrays, or phased arrays. The number and arrangement of transducer elements included in the sensor array 112 may vary in different examples. For instance, the ultrasound sensor array 112 may include a 1D or 2D array of transducer elements, corresponding to linear array and matrix array probes, respectively. A variety of users, e.g., novice sonographers, may handle and operate the ultrasound data acquisition unit 110 to perform the methods described herein.

The data acquisition unit 110 may also include a beamformer 120, e.g., comprising a microbeamformer or a combination of a microbeamformer and a main beamformer, coupled to the ultrasound sensor array 112. The beamformer 120 may control the transmission and reception of ultrasound signals such that discernable image data may be produced and processed with the aid of other system components. As described herein, the beamformer 120 may be configured to adjust the ensemble length (for Doppler applications) and temporal smoothing window size (for VFI applications), along with step size of the received echo data in response to recommendations 131 received from the data processor 126. The functions of the beamformer 120 may vary in different ultrasound probe varieties. For example, the beamformer 120 may comprise two separate beamformers: a transmit beamformer configured to receive and process pulsed sequences of ultrasonic energy for transmission into a subject, and a separate receive beamformer configured to amplify, delay and/or sum received ultrasound echo signals. In some embodiments, the beamformer 120 may include a microbeamformer operating on groups of sensor elements for both transmit and receive beamforming, coupled to a main beamformer which operates on the group inputs and outputs for both transmit and receive beamforming, respectively. In particular embodiments, the microbeamformer may control the transmission and reception of signals by the transducer elements in the array. The ensemble length, expressed by the number of sample signals used for averaging flow velocity, may vary, ranging from about 2 to about 16, about 4 to about 14, about 6 to about 12, or about 8 to about 10.

The signal processor 122 may be communicatively, operatively and/or physically coupled with the sensor array 112 and/or the beamformer 120. In the example shown in FIG. 1, the signal processor 122 is included as an integral component of the data acquisition unit 110, but in other examples, the signal processor 122 may be a separate component. In some examples, the signal processor may be housed together with the sensor array 112 or it may be physically separate from but communicatively (e.g., via a wired or wireless connection) coupled thereto. The signal processor 122 may be configured to receive unfiltered and disorganized ultrasound data embodying the ultrasound echoes 118 received at the sensor array 112. From this data, the signal processor 122 may continuously generate a plurality of ultrasound image frames 124 as a user scans the ROI 116.

The data processor 126 may receive and process ultrasound data, e.g., ultrasound image frames 124, generated by the ultrasound data acquisition unit 110. Based on the received data, the data processor 126 can continuously, e.g., on a frame-by-frame basis, determine mean flow velocity magnitude and acceleration. In various implementations, the data processor 126 may receive and process a sequence of temporally discrete echo signals from different points in an image field or window, e.g., sample volume 119. From each ensemble of received echoes defined by the beamformer 120, the data processor 126 can estimate the Doppler shift frequency of flowing blood, for example, and thereby determine mean blood flow velocity magnitude as a function of time. In various examples, the mean flow velocity magnitude can be estimated by implementing autocorrelation or multi-step velocity estimation techniques. The data processor 126 can make this determination within specified spatial, temporal, or spatiotemporal windows, which can encompass an entire flow region or specific sub-regions thereof. The windows can also be locally and/or spatiotemporally adaptive. From the determined mean velocity magnitude, the acceleration can also be elucidated by determining the change in velocity magnitude over time.

At measured peak flow velocities, e.g., systole, the flow signal SNR may be high, making it easier to distinguish targeted flow from background clutter. Since the flow acceleration may also be high, higher temporal resolution (frame rate) is required to better resolve the peak flow. Consequently, shorter ensemble lengths and shorter step sizes may be suitable for high mean velocities. By contrast, at low flow velocities, e.g., diastole, the flow signal SNR may be relatively low, making it more difficult to distinguish targeted flow from background clutter. Flow acceleration may also be lower at lower flow velocities. As a result, longer ensemble lengths (i.e., less temporal resolution) and step sizes may be more suitable during periods of slower flow to increase the flow signal SNR. Accordingly, the optimal ensemble lengths and step sizes for processing flow having higher flow velocity magnitudes and accelerations may not be suitable for processing flow having lower flow velocity magnitudes or accelerations, and vice versa.

To correct for the cyclical fluctuations between high and low flow velocity magnitudes and accelerations that may characterize pulsatile flow within the ROI 116, the data processor 126 can adaptively determine adjusted ensemble lengths, step sizes, and/or additional imaging parameters based on repeated mean flow velocity magnitude and acceleration measurements. To increase the SNR, higher mean velocity magnitudes may prompt the data processor 126 to recommend shorter ensemble lengths, e.g., about 4 to about 6, and lower mean velocity magnitudes may prompt the data processor 126 to recommend longer ensemble lengths, e.g., about 12 to about 16. Similarly, high flow acceleration values may prompt the data processor 126 to recommend shorter step sizes, e.g., about 1 to about 2, and lower flow acceleration may prompt the data processor 126 to recommend longer step sizes, e.g., about 3 to about 6. The particular manner in which the data processor 126 is configured to determine recommended ensemble lengths and step sizes may vary. In one simplified example, a recommended ensemble length may be determined according to the following equation:

$$L = \frac{L_{min} L_{max} (v_{max} v_{min})}{(L_{max} - L_{min})v + L_{min} v_{max} - L_{max} v_{min}} \quad \text{(Equation 1.1)}$$

where L is ensemble length at a given mean flow velocity v, $L_{min}$ is the minimum ensemble length of the ultrasound acquisition unit, $L_{max}$ is the maximum ensemble length of the ultrasound acquisition unit, $v_{min}$ is the minimum mean flow velocity, and $v_{max}$ is the maximum mean flow velocity.

For VFI applications, temporal smoothing filter lengths (analogous to ensemble lengths in Doppler systems) may be performed on slow-time to increase flow signal SNR. Longer temporal smoothing filter lengths may be implemented to increase flow signal SNR; however, temporal resolution (or frame rates, which are typically high during VFI) decreases with longer temporal smoothing filter lengths. Accordingly, the SNRs generated through VFI applications may drop in a manner analogous to Doppler systems during pulsatile flow analysis. The data processor 126 can operate in a similar manner during implementation of VFI modalities, e.g., by adjusting the temporal smoothing filter lengths in response to measured mean flow velocity magnitudes.

The data processor 126 may also be configured to determine one or more additional flow imaging parameter adjustments in response to the determined velocity and/or acceleration values. For example, the data processor 126 can determine necessary transmit parameter adjustments, such as adjustments to the central frequency and bandwidth of color transmit pulses. In addition or alternatively, the data processor 126 can adjust the number, central frequency, and/or passband of a QBP filter applied to the input radiofrequency signals. The data processor 126 may also be configured to adjust the type, order, central frequency, and/or passband of a wall filter applied to each color IQ ensemble. The data processor 126 may also be configured to determine one or more post-processing parameter adjustments, including adjustments to spatial smoothing parameter (s) and/or color priority (and other flash suppression) parameters.

After determining a recommended ensemble length and step size (alone or in addition to one or more additional flow imaging parameter adjustments) for a given mean flow velocity magnitude and acceleration value, the data processor 126 can communicate the recommendation 131 back to the data acquisition unit 110, which can then update the acquisition settings to implement the recommended changes accordingly. Recommendations 131 can be generated by the data processor 126 on a frame-by-frame basis, such that in some examples, about 30 recommendations 131 are determined and implemented by the data acquisition unit 110 per second. In various embodiments, each of the adjustments determined by the data processor 126 can be communicated to the system component configured to implement the adjustments. For example, filter adjustments can be communicated to the appropriate filter, which may constitute a sub-module of the signal processor 122 or data processor 126. Pulse transmittal adjustments can be communicated to one or more components of the data acquisition unit 110, such as the beamformer 120 or the ultrasound sensor array 112. In this manner, parameter adjustments determined by the data processor 126 are used to adjust the operation of the system 100.

The particular configuration of the processors involved in determining mean flow velocity magnitude and acceleration, determining the ensemble length and step size recommendations, and implementing the recommendations can vary. For example, the data processor 126 may coordinate with the signal processor 122 and/or the beamformer 120, or the data processor 126, signal processor 122 and/or beamformer may constitute integral processing components, all within the data acquisition unit 110. As mentioned above, the data processor 126 may include distinct sub-modules configured to determine flow properties and adaptive acquisition settings separately. Such sub-modules may include the flow property module 128 and the parameter adjustment module 130.

The display processor 132 and graphical user interface 134 can be configured to organize and display color Doppler, spectral Doppler, VFI data, and/or B-mode image data to form velocity color flow images and/or power Doppler images, which may be displayed concurrently, e.g., overlaying, B-mode images 136 of the ROI 116. The measured velocity and/or acceleration values can be mapped to color values by the display processor 132, which can spatially arrange the color values in the desired image format. The color values can then be displayed as pixels on the graphical user interface 134, each color representing a specific velocity of flow in a particular flow direction. The color flow velocity information can also be overlaid onto B-mode imagery of anatomical structures within the ROI 116. The graphical user interface 134 can be configured to display one or more user notifications and/or elements 140 selectable by a user. For instance, such elements 140 displayed by the graphical user interface 134 may include an "Auto Optimize" graphic, the selection of which can invoke the adaptive adjustments to ensemble length and step size described herein.

Figure 2:
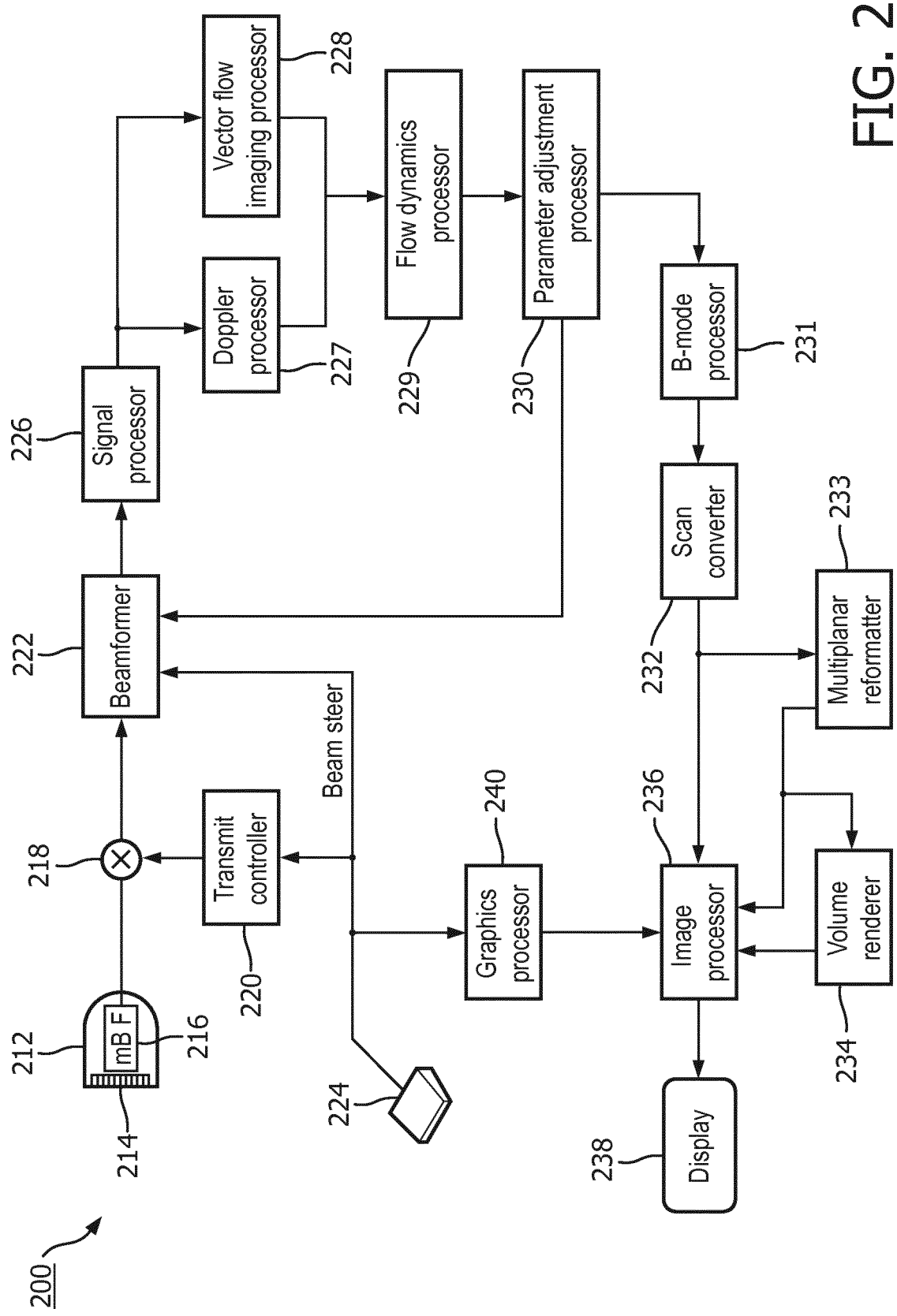
FIG. 2 is a block diagram of another ultrasound system in accordance with an embodiment of the present disclosure.

FIG. 2 is a block diagram of another ultrasound system 200 in accordance with an embodiment of the present disclosure. One or more components shown in FIG. 2 may be included within a system configured to determine mean flow velocity magnitude and acceleration values, and adjust the ensemble length (or temporal smoothing filter length) and step size accordingly. For example, any of the above-described functions of the signal processor 122 or data processor 126 may be implemented and/or controlled by one or more of the processing components shown in FIG. 2, including for example, signal processor 226, Doppler processor 227, Vector Flow Imaging processor 228, flow dynamics processor 229, parameter adjustment processor 230, B-mode processor 231, scan converter 232, multiplanar reformatter 233, volume renderer 234 and/or image processor 236.

In the ultrasonic imaging system of FIG. 2, an ultrasound probe 212 includes a transducer array 214 for transmitting ultrasonic waves into a region containing a feature harboring flow, e.g., a vein or artery, and receiving echo information responsive to the transmitted waves. In various embodiments, the transducer array 214 may be a matrix array or a 2D phased array. The transducer array may be coupled to a microbeamformer 216 in the probe 212 which may control the transmission and reception of signals by the transducer elements in the array. In the example shown, the microbeamformer 216 is coupled by the probe cable to a transmit/receive (T/R) switch 218, which switches between transmission and reception and protects the main beamformer 222 from high energy transmit signals. In some embodiments, the T/R switch 218 and other elements in the system can be included in the transducer probe rather than in a separate ultrasound system component. The transmission of ultrasonic beams from the transducer array 214 under control of the microbeamformer 216 may be directed by the transmit controller 220 coupled to the T/R switch 218 and the beamformer 222, which can receive input, e.g., from the user's operation of a control panel or user interface 224 or from the parameter adjustment processor 230. A function that may be controlled by the transmit controller 220 is the direction in which beams are steered. Beams may be steered straight ahead from (orthogonal to) the transducer array, or at different angles for a wider field of view. The partially beamformed signals produced by the microbeamformer 216 are coupled to a main beamformer 222 where partially beamformed signals from individual patches of transducer elements are combined into a fully beamformed signal.

The beamformed signals may be communicated to a signal processor 226. The signal processor 226 may process the received echo signals in various ways, such as bandpass filtering, decimation, I and Q component separation, and/or harmonic signal separation. The signal processor 226 may also perform additional signal enhancement via speckle reduction, signal compounding, and/or noise elimination. In some examples, data generated by the different processing techniques employed by the signal processor 226 may be used by the flow dynamics processor 229 to determine mean flow velocity magnitude and/or acceleration. Signals processed by the signal processor 226 may be communicated to a Doppler processor 227 or a Vector Flow Imaging processor 228, depending on the specific system employed. A flow dynamics processor 229 may then determine the mean flow velocity magnitude and acceleration, which are then communicated to the parameter adjustment processor 230. The parameter adjustment processor 230 can be configured to determine an adjusted ensemble length and step size for each signal, determinations which can then be communicated back to the beamformer 222 for implementation. Additional parameter adjustment(s) can also be determined by the parameter adjustment processor 230, as discussed above. The processed signals may also be communicated to a B-mode processor 231, which may employ amplitude detection for imaging structures in the body. The signals produced by the B-mode processor 231 may be coupled to a scan converter 232 and a multiplanar reformatter 233. The scan converter 232 may arrange the echo signals in the spatial relationship from which they were received in a desired image format. For instance, the scan converter 232 may arrange the echo signals into a two dimensional (2D) sector-shaped format. The multiplanar reformatter 233 may convert echoes which are received from points in a common plane in a volumetric region of the body into an ultrasonic image of that plane, as described in U.S. Pat. No. 6,443,896 (Detmer). In some examples, a volume renderer 234 may convert the echo signals of a 3D data set into a projected 3D image as viewed from a given reference point, e.g., as described in U.S. Pat. No. 6,530,885 (Entrekin et al.). The 2D or 3D images may be communicated from the scan converter 232, multiplanar reformatter 233, and volume renderer 234 to an image processor 236 for further enhancement, buffering and/or temporary storage for display on an image display 238.

A graphics processor 240 can generate graphic overlays for display with the ultrasound images. These graphic overlays may contain, e.g., standard identifying information such as patient name, date and time of the image, imaging parameters, and the like, and also various outputs generated by the flow dynamics processor 229. In some examples, the graphics processor may receive input from the user interface 224, such as a typed patient name or confirmation that an instruction displayed or emitted from the interface has been acknowledged by the user of the system 200. The user interface 224 may also receive input regarding the selection of particular imaging modalities and the operating parameters included in such modalities, input prompting adjustments to the settings and/or parameters used by the system 200, input requesting additional instructions or assistance for performing an ultrasound scan, and/or input requesting that one or more ultrasound images be saved and/or transmitted to a remote receiver. The user interface may also be coupled to the multiplanar reformatter 233 for selection and control of a display of multiple multiplanar reformatted (MPR) images.

Figure 3:
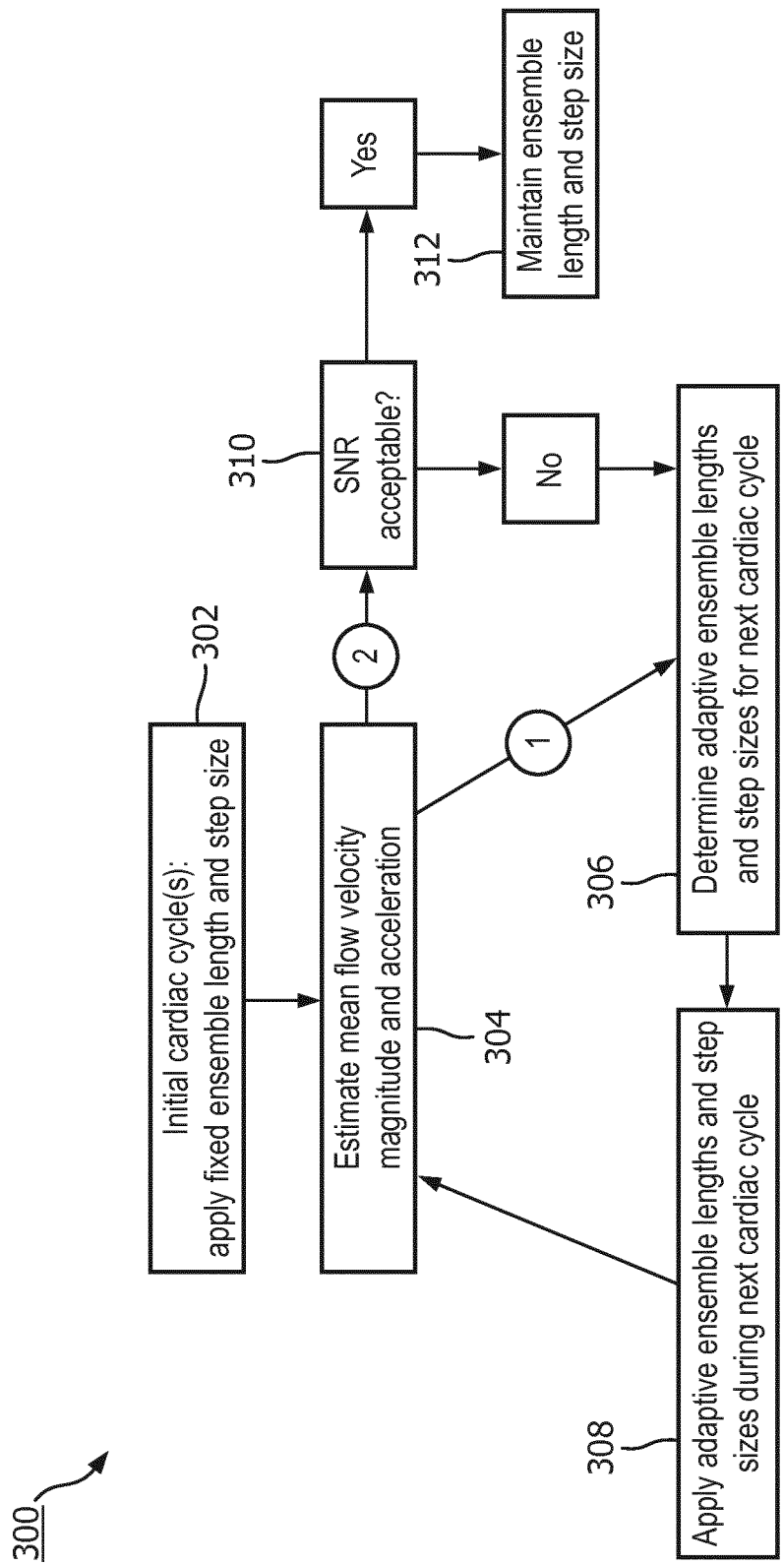
FIG. 3 is a block diagram of a mode of operation implemented by one or more processors in accordance with an embodiment of the present disclosure.

FIG. 3 is a block diagram of a mode of operation implemented by one or more processors described herein. As shown, systems herein can implement a corrective feedback loop 300 configured to iteratively adjust ensemble length (and smoothing filter length for VFI) and step size in response to recurring measurements of mean flow velocity magnitude and acceleration, respectively. Adjustments to one or more additional flow imaging parameters, e.g., wall/clutter filter settings, can also be implemented via the corrective feedback loop 300. In some examples, the feedback loop 300 may be coordinated with a patient's cardiac cycle, such that adjustments to ensemble length, step size, and/or other parameters can be made with the onset of each cycle, to the extent necessary. In addition or alternatively, the feedback loop 300 may be aligned with a looped series of image frames or a time window selected manually by a user or automatically by the system.

In some embodiments, fixed settings of ensemble length and step size can be implemented during an initial period 302 lasting for a finite number of cardiac cycles, e.g., between 1, 2, 3, 4 or more cardiac cycles. Mean flow velocity magnitudes and accelerations can then be estimated in an estimation step 304 using the data acquired during the initial period 302. Based on the mean flow velocity magnitudes and accelerations, adaptive ensemble lengths and step sizes, respectively, can be determined in a parameter adjustment step 306 for the next cardiac cycle, loop or time-window lasting between about 0.5 to 2 seconds, for example. The number of discrete parameter adjustments determined can depend on the frame rate. For example, for a 1-second cardiac cycle, systems operating at 30 frames per second may be configured to acquire 30 mean velocity magnitudes and accelerations during a given estimation step 304. Example frame rates, and thus flow parameter adjustment rates, may vary, ranging from about 15 to about 60 Hz in various embodiments. The new, adaptive ensemble lengths and step sizes can then be implemented for flow processing during the next cardiac cycle, loop or time-window in an implementation step 308. In some embodiments, adjustments to ensemble length and step size can be paired with automatic adjustments to one or more downstream data acquisition parameters including, for example, settings of a wall filter and/or clutter filter included in the system.

The system again determines mean velocity magnitude and acceleration values during the estimation step 304, which can be used to adjust the adaptive ensemble lengths and step sizes for the next cardiac cycle. The feedback loop 300 thus iteratively adjusts the ensemble length and/or step size in response to cyclical updates to mean flow velocity magnitude and acceleration. The first pass through the feedback loop (labeled "1" in FIG. 3) may proceed as indicated, and during a second pass through the feedback loop (labeled "2"), an evaluation step 310 can be implemented to determine whether the feedback loop 300 needs to continue. The evaluation step 310 can involve examining a SNR using signals acquired during the estimation step 304. In some examples, the SNR can be compared to a threshold value. If the measured SNR is above the threshold value, the current ensemble length and step size can be maintained by placing a hold 312 on further adjustments. In some examples, if the measured SNR is above the threshold value, the current ensemble length may be reduced to achieve higher frame rates and improve temporal resolution of the system. Ensemble length reduction may be implemented if the measured SNR exceeds the threshold value by a particular amount in some embodiments. For example, SNR values exceeding the threshold by about 10%, 20%, 30%, 40%, 50% or more may trigger a concomitant reduction in ensemble length, while SNR values exceeding the threshold by less than 10%, 5%, 2%, or 1% may trigger the hold 312. If the measured SNR is below the threshold value, the feedback loop 300 may continue to the parameter adjustment step 306 to further improve the applied ensemble lengths and/or step sizes. If the imaging condition is stable, e.g. maximum and minimum velocities remain relatively constant across one or more cycles of pulsatile flow, adaptive ensemble lengths and step sizes may converge to an approximately steady state over the course of a measured cycle and acquired SNRs may improve, thus increasing the likelihood of triggering a hold 312 in the feedback loop. If the imaging condition changes, e.g., pulsatile flow becomes inconsistent, the feedback loop 300 will likely continue, iteratively measuring mean flow velocity magnitude and acceleration and updating ensemble length and step size accordingly until the imaging parameters consistently converge and a satisfactory SNR is attained. In embodiments, the evaluation step 310 may involve comparing an acquired SNR to an SNR variance threshold. In addition or alternatively, the evaluation step 310 may involve comparing acquired flow measurements and/or adjusted acquisition parameters across cardiac cycles. According to such examples, a hold 312 may be triggered upon reaching a defined level of cross-cycle consistency. For example, a cross-cycle change in adapted ensemble length and/or step size of less than about 1-5% may trigger initiation of the hold 312. By regularly evaluating the performance of the feedback loop 300, systems herein may reduce the computational load required of one or more processors, thereby also improving processing time and overall workflow efficiency.

The feedback loop 300 may be initiated automatically, for example every few seconds or every few cardiac cycles. In some examples, the feedback loop 300 can be initiated in response to a user selection of an automatic optimization feature displayed on a graphical user interface, e.g., interface 134. The feedback loop 300 can also be automatically initiated each time the user repositions the sample volume or adjusts a color box displayed on the graphical user interface 134. To ensure that each cardiac cycle, loop, or specific time-window is recognized, separated, and analyzed independently, systems herein can implement or be responsive to ECG gating, user definition, or flow pattern recognition.

Figure 4A:
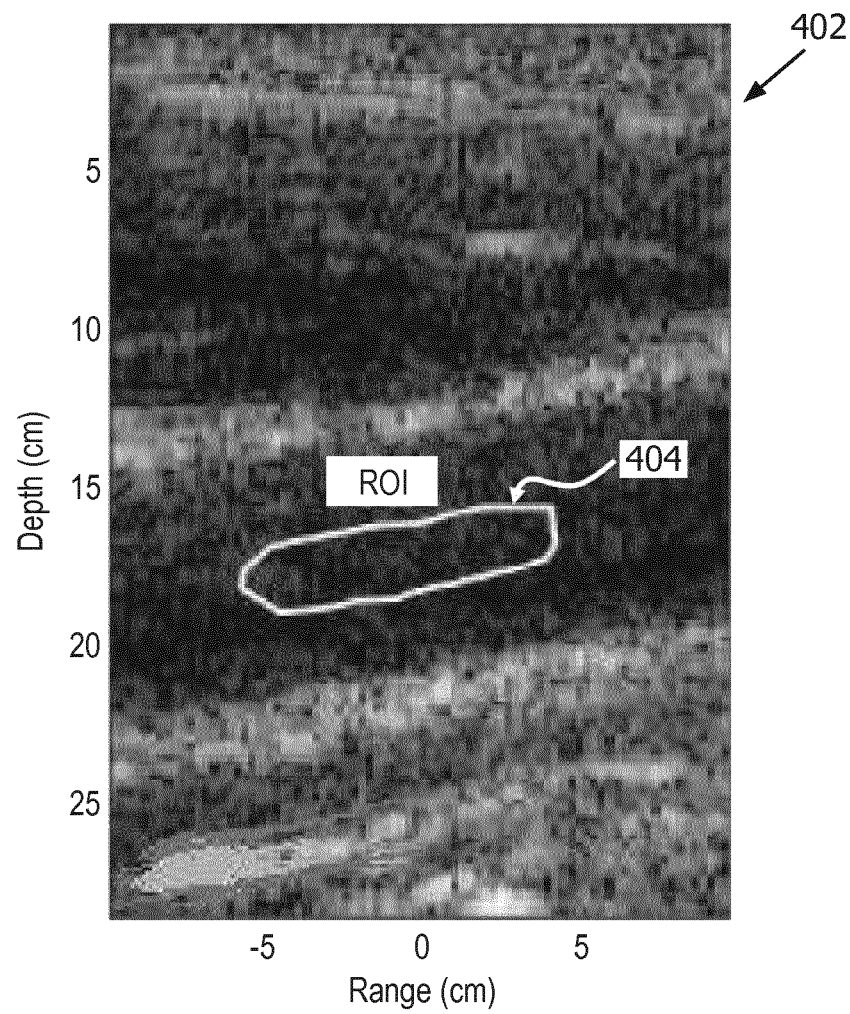
FIG. 4A is a B-mode image of a region of a human carotid artery captured in accordance with an embodiment of the present disclosure.
Figure 4B:
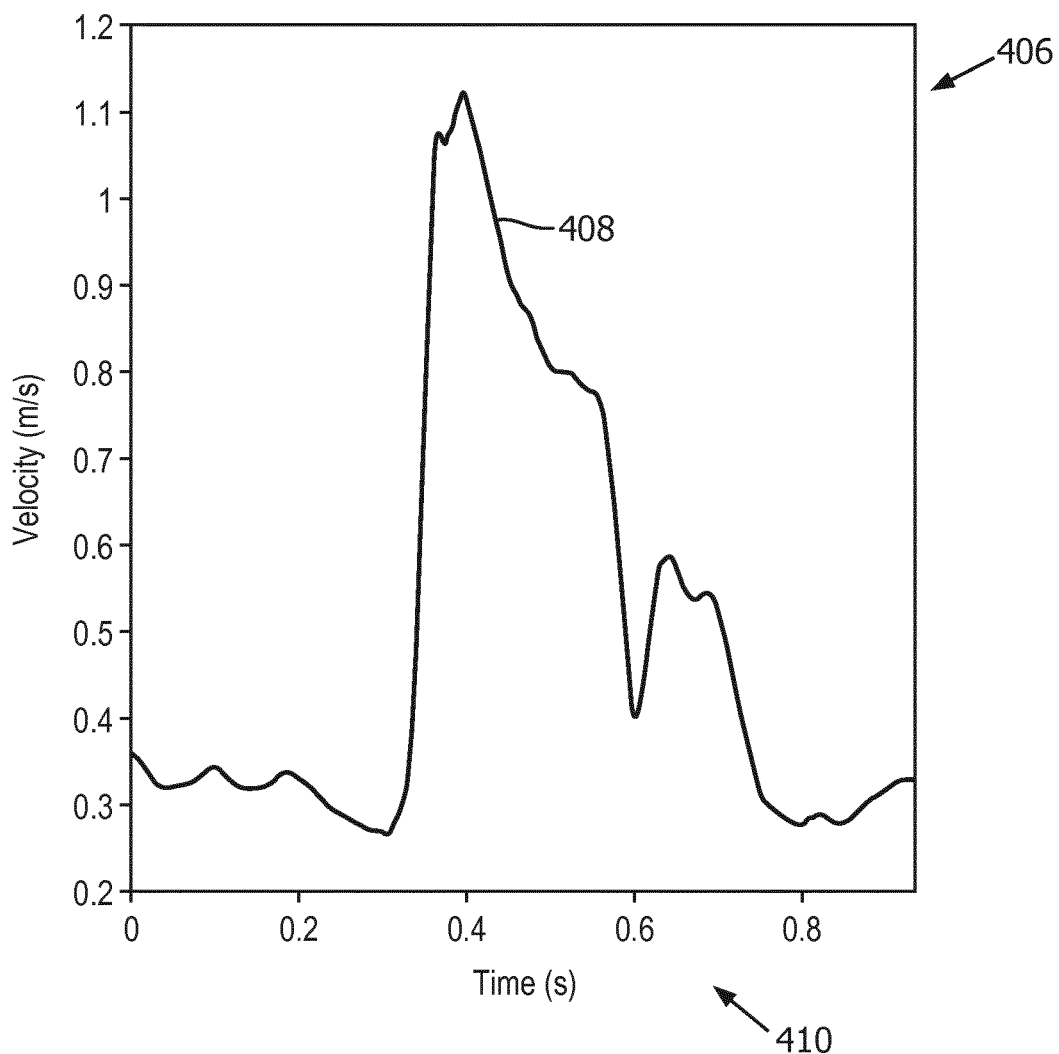
FIG. 4B is a graph of mean flow velocity magnitude determined within the region of interest identified in FIG. 4A in accordance with an embodiment of the present disclosure.
Figure 4C:
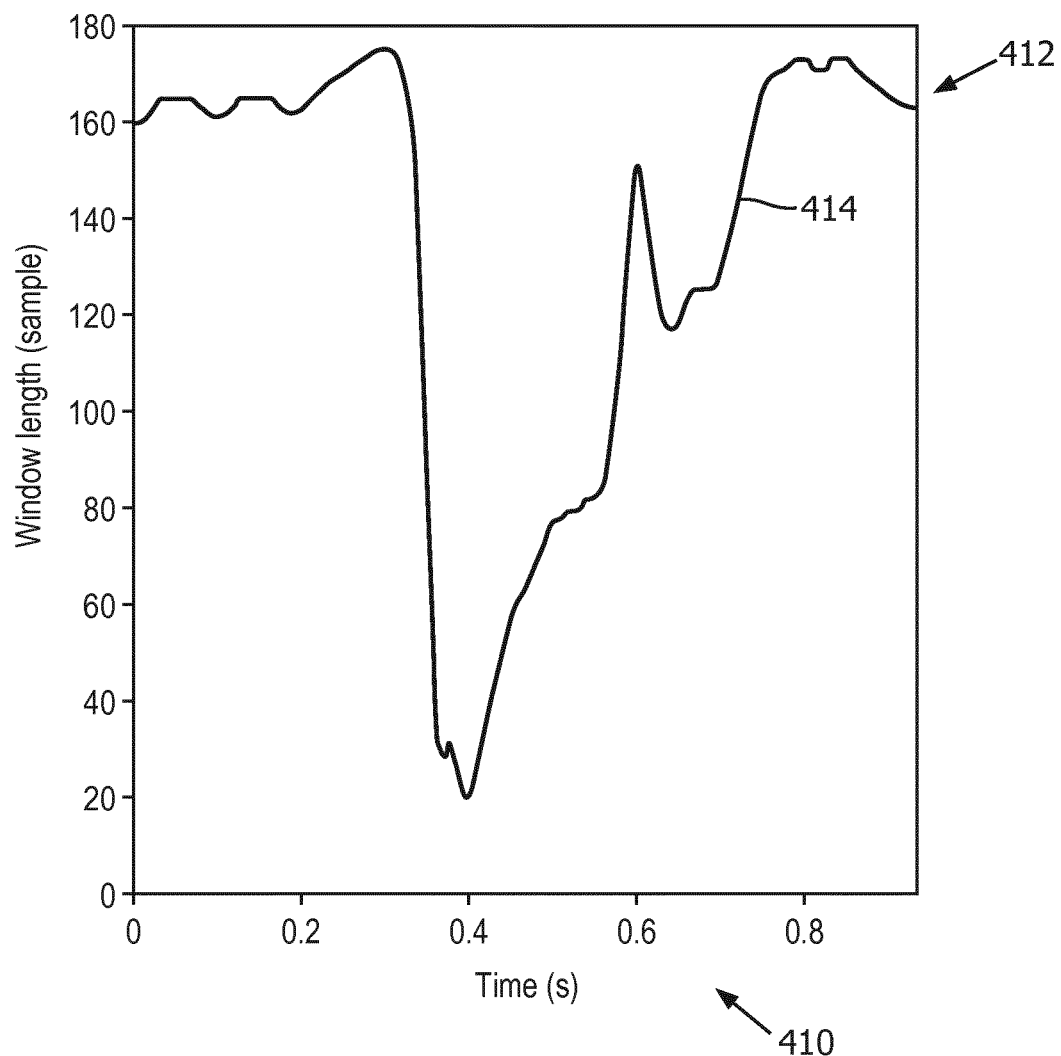
FIG. 4C is a graph of adaptive ensemble length determined based on the graph of FIG. 4B in accordance with an embodiment of the present disclosure.

FIG. 4A is an example of a B-mode image 402 of a carotid artery captured by systems described herein. The image 402 includes a labeled ROI 404, within which one or more flow properties may be determined. In some examples, flow data such as color flow Doppler data and/or spectral data, may be displayed over the B-mode image 402, along with a color box. The ROI 404 may be defined by a user, for example by specifying the ROI boundaries on a user interface displaying the image 402. FIG. 4B is a graph 406 of mean flow velocity magnitude 408 determined in a single acquisition phase 410 within the ROI 404 shown in FIG. 4A. The acquisition phase 410 in this particular example spans 1 second, or about 1 cardiac cycle. As shown, the mean flow velocity magnitude 408 remains relatively low, e.g., less than 0.4 m/s, for the first ~0.3 seconds, and then spikes to about 1.1 m/s before receding. In accordance with the principles described herein, the optimal ensemble lengths and step sizes applied to such differing velocity magnitudes will vary. FIG. 4C is a graph 412 of adaptive ensemble lengths 414 determined using the velocity data of FIG. 4B. As shown, the recommended ensemble lengths 414 are generally greater for lower velocity magnitudes and lesser for higher velocity magnitudes. By tracking velocity magnitude during pulsatile flow and adaptively adjusting the ensemble length based on the velocity magnitude data, systems herein can apply improved or even optimal imaging parameters to received ultrasound echoes, regardless of flow velocity and/or acceleration.

Figure 5:
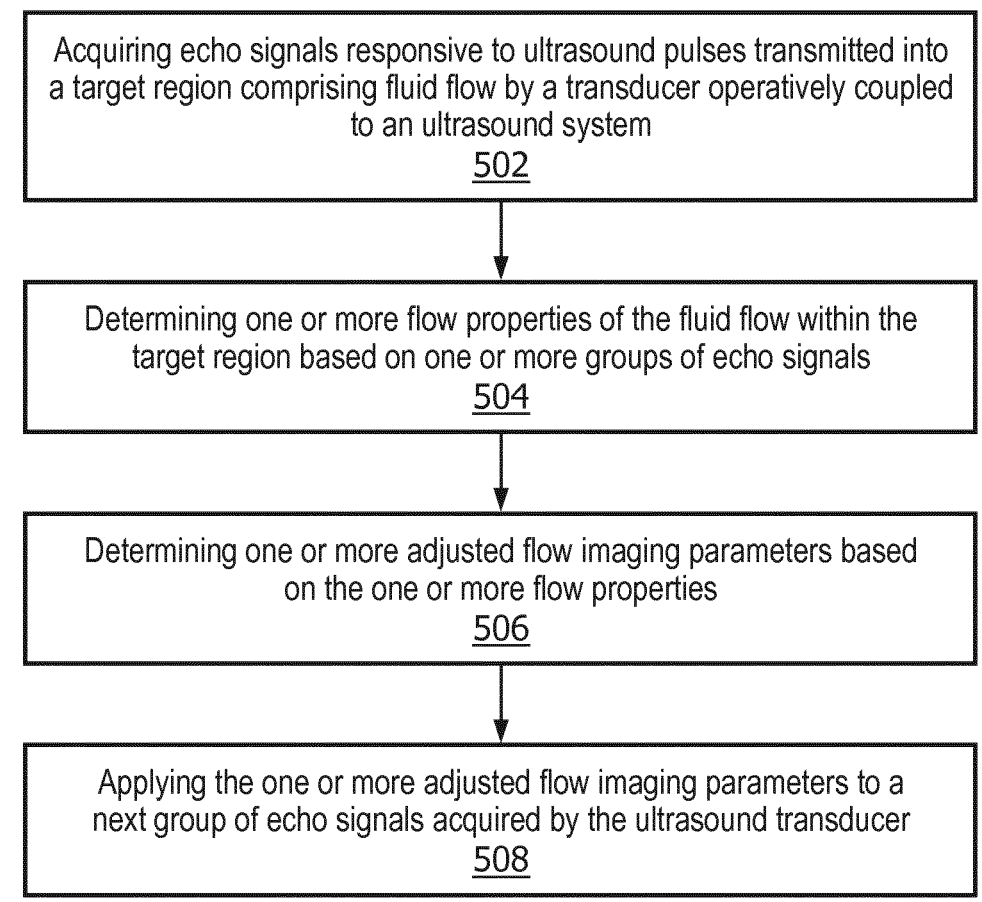
FIG. 5 is a flow diagram of a method of ultrasound imaging performed in accordance with an embodiment of the present disclosure.

FIG. 5 is a flow diagram of a method of ultrasound flow imaging performed in accordance with principles of the present disclosure. The example method 500 shows the steps that may be utilized, in any sequence, by the systems and/or apparatuses described herein for acquiring flow data and adaptively adjusting one or more flow imaging parameters in response to the data. The method 500 may be performed by an ultrasound imaging system, such as system 100, or other systems including, for example, a mobile system such as LUMIFY by Koninklijke Philips N.V. ("Philips"). Additional example systems may include SPARQ and/or EPIQ, also produced by Philips.

In the embodiment shown, the method 500 begins at block 502 by "acquiring echo signals responsive to ultrasound pulses transmitted into a target region comprising fluid flow by a transducer operatively coupled to an ultrasound system."

At block 504, the method involves "determining one or more flow properties of the fluid flow within the target region based on one or more groups of echo signals."

At block 506, the method involves "determining one or more adjusted flow imaging parameters based on the one or more flow properties."

At block 508, the method involves "applying the one or more adjusted flow imaging parameters to a next group of echo signals acquired by the ultrasound transducer."

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
an ultrasound transducer configured to acquire echo signals responsive to ultrasound pulses transmitted toward a target region comprising fluid flow;
one or more processors in communication with the ultrasound transducer and configured to:
    determine one or more flow properties of the fluid flow on a frame-by-frame basis within the target region based on one or more groups of echo signals acquired during a first acquisition phase, wherein the one or more flow properties comprise a mean flow velocity magnitude and an acceleration; and
    determine one or more adjusted flow imaging parameters based on the one or more flow properties, wherein the one or more adjusted flow imaging parameters comprise an adjusted ensemble length and an adjusted step size, and wherein step size is related to flow acceleration or deceleration and is used for autocorrelation estimation; and
a beamformer coupled with the ultrasound transducer and configured to apply the one or more adjusted flow imaging parameters on a frame-by-frame basis when obtaining a next group of echo signals acquired by the ultrasound transducer during a second acquisition phase.

2. The ultrasound imaging system of claim 1, wherein the one or more processors are further configured to determine a signal-to-noise ratio (SNR) based on the one or more groups of echo signals.

3. The ultrasound imaging system of claim 2, wherein the one or more processors are further configured to compare the SNR to a threshold value, and:
if the SNR is not greater than the threshold value, repeat the steps of:
determining the one or more flow properties of the fluid flow on a frame-by-frame basis within the target region based on the one or more groups of echo signals acquired during the first acquisition phase; and
determining the one or more adjusted flow imaging parameters based on the one or more flow properties; and
if the SNR is greater than the threshold value, place a hold on additional flow imaging parameter adjustments.

4. The ultrasound imaging system of claim 1, further comprising a graphical user interface configured to display a selectable graphic for initiating the one or more processors.

5. The ultrasound imaging system of claim 4, wherein the graphical user interface is further configured to display the one or more flow properties and/or the one or more adjusted flow imaging parameters.

6. The ultrasound imaging system of claim 4, wherein the graphical user interface is configured to display a SNR based on the one or more groups of echo signals.

7. The ultrasound imaging system of claim 1, wherein the first acquisition phase comprises 1 to 4 cardiac cycles, inclusive.

8. The ultrasound imaging system of claim 1, wherein the first acquisition phase and the second acquisition phase together comprise consecutive cardiac cycles.

9. The ultrasound imaging system of claim 1, wherein the one or more groups of echo signals comprise a plurality of groups of echo signals, and wherein between 15 and 60 groups of echo signals of the plurality of groups of echo signals are acquired per second.

10. A method of ultrasound imaging, the method comprising:
acquiring echo signals responsive to ultrasound pulses transmitted into a target region comprising fluid flow by an ultrasound transducer operatively coupled to an ultrasound system;
determining one or more flow properties of the fluid flow on a frame-by-frame basis within the target region based on one or more groups of echo signals;
determining one or more adjusted flow imaging parameters based on the one or more flow properties, wherein the one or more adjusted flow imaging parameters comprise an adjusted ensemble length and an adjusted step size, and wherein step size is related to flow acceleration or deceleration and is used for autocorrelation estimation; and
applying the one or more adjusted flow imaging parameters on a frame-by-frame basis when obtaining a next group of echo signals acquired by the ultrasound transducer.

11. The method of claim 10, wherein the one or more flow properties comprise a mean flow velocity magnitude and an acceleration.

12. The method of claim 10, further comprising determining and displaying a SNR based on the one or more groups of echo signals.

13. The method of claim 12, further comprising comparing the SNR to a threshold value, and:
if the SNR is not greater than the threshold value, repeating the steps of:
determining the one or more flow properties of the fluid flow on a frame-by-frame basis within the target region based on the one or more groups of echo signals acquired during a first acquisition phase; and
determining the one or more adjusted flow imaging parameters based on the one or more flow properties; and
if the SNR is greater than the threshold value, placing a hold on additional flow imaging parameter adjustment.

14. The method of claim 10, further comprising displaying the one or more flow properties and/or the one or more adjusted flow imaging parameters.

15. The method of claim 10, further comprising displaying a selectable graphic for initiating the determining of the one or more adjusted flow imaging parameters.

16. A non-transitory computer-readable medium comprising executable instructions, which when executed cause a processor of a medical imaging system to perform the method of claim 13.

* * * * *